United States Patent [19]

Morigaki et al.

[11] 4,388,404
[45] Jun. 14, 1983

[54] SILVER HALIDE COLOR PHOTOGRAPHIC LIGHT-SENSITIVE MATERIAL

[75] Inventors: Masakazu Morigaki; Morio Yagihara; Takashi Ozawa, all of Kanagawa, Japan

[73] Assignee: Fuji Photo Film Co., Ltd., Kanagawa, Japan

[21] Appl. No.: 369,769

[22] Filed: Apr. 19, 1982

[30] Foreign Application Priority Data

Apr. 21, 1981 [JP] Japan .................. 56-60264

[51] Int. Cl.³ ............... G03C 1/40
[52] U.S. Cl. .................. 430/548; 430/372; 430/381; 430/551; 430/554; 430/555; 430/558
[58] Field of Search ............ 430/548, 551, 554, 555, 430/558, 372, 381

[56] References Cited

U.S. PATENT DOCUMENTS

| 3,451,820 | 6/1969 | Umberger | 430/548 |
| 3,926,436 | 12/1975 | Monbaliu et al. | 430/548 |
| 4,179,293 | 12/1979 | Hirano et al. | 430/551 |
| 4,232,114 | 11/1980 | Adachi et al. | 430/372 |

FOREIGN PATENT DOCUMENTS 56-5543 1/1981 Japan .
1347556 2/1974 United Kingdom .

OTHER PUBLICATIONS

Research Disclosure, No. 17825, Feb. 1979.

Primary Examiner—J. Travis Brown
Attorney, Agent, or Firm—Sughrue, Mion, Zinn, Macpeak and Seas

[57] ABSTRACT

A silver halide color photographic light-sensitive material is described containing a magenta color image forming polymer coupler latex and at least one compound represented by the following general formula (I)

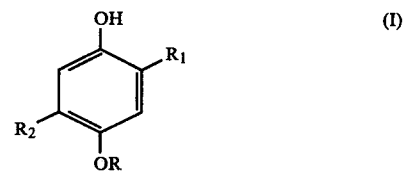

wherein R represents an alkyl group; and $R_1$ and $R_2$ each represents a tertiary alkyl group and $R_1$ and $R_2$ may be the same or different. The disclosed silver halide color photographic light-sensitive material has good film strength, a reduced layer thickness and provides a stable magenta image having an improved sharpness and fastness to light while preventing the formation of yellow stain in non-image areas. A method of forming a color image using the silver halide color photographic light-sensitive material is also described.

25 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material and, particularly, to the improvement in the fastness to light of a color image formed by the reaction of a magenta polymer coupler latex with a primary amine developing agent.

BACKGROUND OF THE INVENTION

A multilayer color photographic light-sensitive material must have each coupler fixed in a separate layer in order to reduce color mixing and improve color reproduction. Many methods for rendering a coupler diffusion-resistant are known. One method is to introduce a long chain aliphatic group into a coupler molecule in order to prevent diffusion. Couplers produced by the method require the addition to an aqueous gelatin solution by solubilizing in alkali, or by dispersing in an aqueous gelatin solution by dissolving in a high boiling organic solvent, since the couplers are immiscible with an aqueous gelatin solution.

Such color couplers may cause crystal formation in a photographic emulsion. When using a high boiling organic solvent, a large amount of gelatin must be employed since the high boiling organic solvent makes the emulsion layer soft. This is counter productive to the requirement that the thickness of the emulsion layer be reduced.

Another method for rendering a coupler diffusion-resistant is to utilize a polymer coupler latex obtained by polymerization of a monomeric coupler. An example of a method of adding a polymer coupler in a latex form to a hydrophilic colloid composition is a method in which a latex prepared by an emulsion polymerization method is directly added to a gelatino silver halide emulsion. In another method a lipophilic polymer coupler obtained by polymerization of a monomeric coupler is dispersed in a latex form in an aqueous gelatin solution. Examples of the former emulsion polymerization method are described in U.S. Pat. No. 3,370,952 U.S. Pat. No. 4,080,211 which respectively describe disbursements in an aqueous gelatin phase and water. An example of the latter method in which a lipophilic polymer coupler is dispersed in a latex form in gelatin is described in U.S. Pat. No. 3,451,820. The method of adding a polymer coupler in a latex form to a hydrophilic colloid composition has many advantages in comparison with other methods. For example, the deterioration of strength of the film formed is small, because the hydrophobic substance is in a latex form. Also, since the latex can contain coupler monomers in a high concentration, it is easy to incorporate couplers in a high concentration into a photographic emulsion, and the increase of viscosity is small. Furthermore, the color mixing is completely prevented, since a polymer coupler is immobilized and the crystallization of couplers in the emulsion layer is small. In particular, when the polymer coupler latex prepared by an emulsion polymerization method is used, the step of adding the coupler to a coating solution can be simplified, since the use of a high boiling organic solvent or an alkali is not necessary and a special dispersing method is not required. Moreover, the thickness of the layer can be reduced, since an organic solvent is not contained therein.

The addition of these polymer couplers in a latex form to a gelatino silver halide emulsion are described, for example in U.S. Pat. Nos. 4,080,211, 3,370,952 and 3,451,820, a copolymer latex with a competitive coupler in West German Pat. No. 2,725,591, and a cyan polymer coupler latex in U.S. Pat. No. 3,767,412.

However, these polymer coupler latexes have a number of problems in addition to the many advantages described above. It would of course be desirable to overcome these problems. The problems include the following:

1. The light fastness of the magenta color image is very poor.
2. Undesirable fog is readily formed upon color development.
3. The fastness to humidity and heat of the color image is poor.
4. The aggregation of latex occurs in a solution.

Various methods for the prevention of fading of a magenta color image caused by light have been provided. Of these methods, the method in which a phenolic compound provided for an oil-soluble magenta coupler is used together with a coupler is extremely effective. Useful phenolic compounds include alkoxy or aryloxy phenols, hydroxycumaranes, hydroxychromans and dihydroxyspirochromans as described in U.S. Pat. Nos. 3,432,300, 3,573,050, 3,574,627 and 3,764,337, West German Patent Application (OLS) No. 2,146,668, etc. Furthermore, in order to prevent the reduction of color density obtained due to these phenolic compounds, the use of a hydroquinone together with the phenolic compound is described in Japanese Patent Application (OPI) No. 14023/76 (the term "OPI" as used herein refers to a "published unexamined Japanese patent application").

However, when the above described compounds are dissolved in water or an organic solvent such as a lower alcohol and then added to a polymer coupler latex, or the compounds are added thereto as a dispersion, the compounds do not improve fastness to light to the same extent that they provide the effect to the oil-soluble magenta couplers. Therefore, as an improved method for the addition of a fading preventing agent, a method in which a phenolic compound having an ether bond at the p-position and a hydroquinone are together loaded into magenta polymer coupler latex particles is described in Japanese Patent Application (OPI) No. 5543/81. However, in order to effectively carry out the loading, it is necessary to mix an emulsion prepared by dispersing a phenolic compound and a hydroquinone in an aqueous gelatin solution with a polymer coupler latex and to stir the mixture at a high temperature of not less than 60° C. for a period of not less than 2 hours. Accordingly, it is clear that preparation is rather difficult.

SUMMARY OF THE INVENTION

An object of the present invention is to provide a color photographic light-sensitive material which provides a magenta color image having an excellent fastness to light using a magenta polymer coupler latex which has the various advantages described above.

Another object of the present invention is to provide a color photographic light-sensitive material which provides a color image which prevents yellow stain in the areas of no or low optical density.

Another object of the present invention is to provide a stabilizer for a color image which does not cause inferior dispersion or which does not crystallize after coating the emulsion.

Still another object of the present invention is to provide a color photographic light-sensitive material which forms a color image which prevents the formation of undesirable color fog.

A further object of the present invention is to provide a color photographic light-sensitive material having good film strength.

A still further object of the present invention is to provide a color photographic light-sensitive material having a reduced layer thickness and an improved sharpness.

Other objects of the present invention will be apparent from the following detailed description and examples.

As a result of extensive investigations, it has now been found that these objects of the present invention are accomplished by the use of a p-alkoxyphenol having tertiary alkyl groups at the 2- and 5-positions thereof as represented by the following general formula (I)

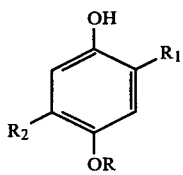

wherein R represents an alkyl group; and $R_1$ and $R_2$ each represents a tertiary alkyl group and $R_1$ and $R_2$ may be the same or different.

DETAILED DESCRIPTION OF THE INVENTION

By using p-alkoxyphenol, the fastness to light of a magenta color image formed from a magenta polymer coupler latex is greatly improved. Even if the p-alkoxyphenol is not loaded into the magenta polymer coupler latex in a manner different from the phenols specifically illustrated in the above described patent specifications, greatly improved results are obtained.

The use of the compound represented by the general formula (I) together with a 3-anilino-5-pyrazolone type magenta coupler which is an oil-soluble magenta coupler is described in Japanese Patent Application (OPI) No. 124141/80. However, the improvement in the fastness to light by the use of the p-alkoxyphenol compound together with a magenta polymer coupler latex is remarkably large.

The compound having the property of improving the fastness to light of a magenta dye which can be used in the present invention is represented by the following general formula (I)

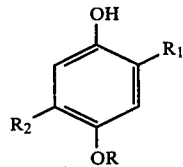

wherein R represents an alkyl group having from 1 to 25 carbon atoms (for example, a methyl group, an ethyl group, an isopropyl group, a tert-butyl group, an octyl group, a dodecyl group, etc.); and $R_1$ and $R_2$ each represents a tertiary alkyl group having from 4 to 20 carbon atoms (for example, a tert-butyl group, a tert-pentyl group, a tert-hexyl group, a tert-octyl group, etc.) and $R_1$ and $R_2$ may be the same or different.

Of the compounds represented by the general formula (I), compounds in which a total number of the carbon atoms included in the alkyl groups represented by R, $R_1$ and $R_2$ is from 9 to 50 are preferred and compounds in which a total number of the carbon atoms included in them is from 10 to 40 are particularly preferred in view of the effects according to the present invention.

The amount of the compound represented by the general formula (I) to be added is in a range from 0.5 mol% to 200 mol%, and preferably 2 mol% to 100 mol%, based on an amount of the coupler monomer included in the polymer coupler.

The compound represented by the general formula (I) is incorporated in a layer containing the magenta color image forming polymer coupler latex and/or a layer adjacent thereto.

Particularly preferred examples of compounds represented by the general formula (I) are set forth below, but the present invention is not to be construed as being limited thereto.

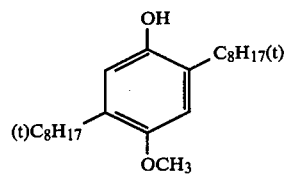

(1)

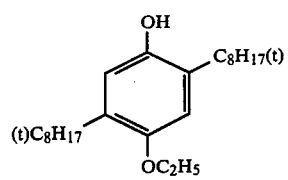

(2)

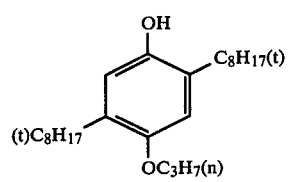

(3)

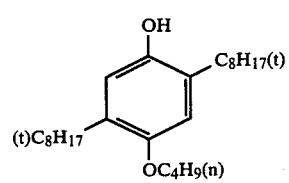

(4)

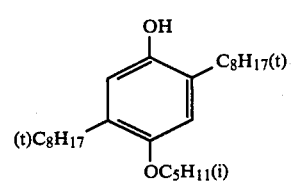

(5)

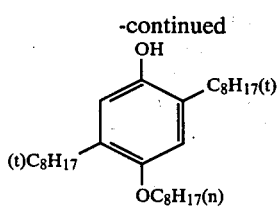 (5)

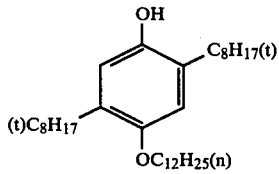 (6)

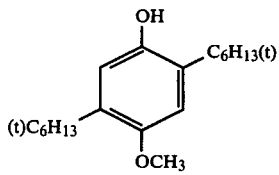 (7)

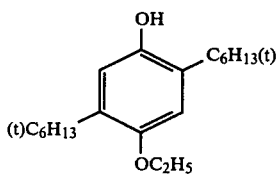 (8)

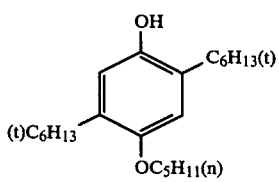 (9)

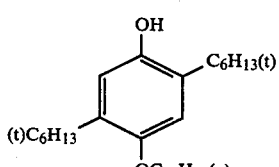 (10)

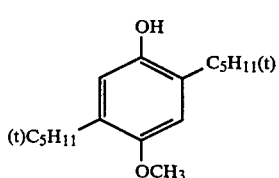 (11)

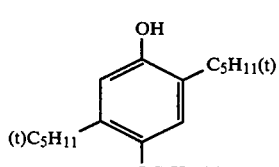 (12)

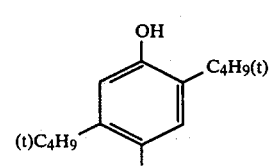 (13)

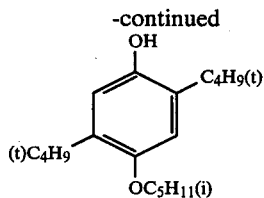 (14)

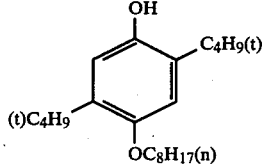 (15)

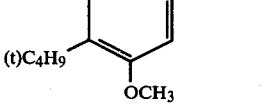 (16)

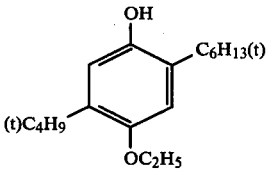 (17)

(18)

The compound according to the present invention can be obtained by alkylation of a 2,5-di-tert-alkylhydroquinone in a conventional manner. Also, it can be obtained by tertiary-alkylation of a p-alkoxyphenol with an olefin, etc. An example of the synthesis is described for reference below.

SYNTHESIS EXAMPLE

Synthesis of Compound (1)

A solution of a mixture of 24.8 g of p-methoxyphenol, 1.5 ml of concentrated sulfuric acid and 10 ml of benzene was kept at 50° C. To this solution, 50 g of 2,4,4-trimethyl-1-pentene was added dropwise over 1 hour. After dropwise addition, the mixture was stirred for 5 hours. After reaction, the product was extracted with benzene, washed with water, neutralized and dried with anhydrous magnesium sulfate. After removing the solvent by distillation, crystals were separated using n-hexane. The crystals were collected by filtration and dried in a reduced pressure to obtain 23.1 g of Compound (1) as colorless crystals.

Melting point: 105° to 106° C.

Elemental Analysis ($C_{23}H_{40}O_2$): Calcd.: C: 79.25% H: 11.57%; Found: C: 79.01% H: 11.60%.

In the practice of the present invention, the compound represented by the general formula (I) can be used individually or as a mixture of two or more thereof. Further, one or more known fade preventing agents can be used together with the compound(s) according to the present invention.

Examples of known fade preventing agents include alkoxy or aryloxy phenols, hydroxycumaranes, hydroxychromans, dihydroxyspirochromans, hydroquinones as described in U.S. Pat. Nos. 3,432,300, 3,573,050, 3,574,627 and 3,764,337 all of which are incorporated herein by reference to disclose such agents, West German Patent Application (OLS) No. 2,146,668, Japanese Patent Application (OPI) No. 14023/76, etc., which are described hereinbefore, and bisphenols as described in Japanese Patent Publication No. 31256/73, U.S. Pat. No. 2,991,177, etc.

The magenta polymer coupler latex which can be used in the present invention is preferably a homopolymer having a repeating unit derived from a monomer coupler represented by the general formula (II) described below, or a copolymer of a repeating unit derived from a monomer coupler represented by the general formula (II) described below and at least one non-color forming monomer having at least one ethylene group which does not have the ability to carry out oxidative coupling with an aromatic primary amine developing agent.

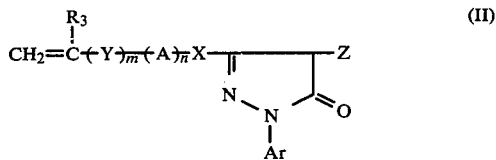

wherein $R_3$ represents hydrogen, a lower alkyl group containing from 1 to 4 carbon atoms, or chlorine; X represents —CONH—, —NH—, —NHCONH— or NHCOO—; Y represents —CONH— or —COO—; A represents an unsubstituted or substituted alkylene group having from 1 to 10 carbon atoms, which may be a straight chain or a branched chain (for example, a methylene group, a methylmethylene group, a dimethylmethylene group, a dimethylene group, a trimethylene group, a decylmethylene group, etc.) or an unsubstituted or substituted phenylene group.

Substituents for the alkylene group or the phenylene group represented by A include an aryl group (for example, a phenyl group, etc.), a nitro group, a hydroxy group, a cyano group, a sulfo group, an alkoxy group (for example, a methoxy group, etc.), an aryloxy group (for example, a phenoxy group, etc.), an acyloxy group (for example, an acetoxy group, etc.), an acylamino group (for example, an acetylamino group, etc.), a sulfonamido group (for example, a methanesulfonamido group, etc.), a sulfamoyl group (for example, a methylsulfamoyl group, etc.), a halogen atom (for example, fluorine, chlorine, bromine, etc.), a carboxy group, a carbamoyl group (for example, a methylcarbamoyl group, etc.), an alkoxycarbonyl group (for example, a methoxycarbonyl group, etc.), a sulfonyl group (for example, a methylsulfonyl group, etc.), and the like. When two or more substituents are present, they may be the same or different.

Ar represents an unsubstituted or substituted phenyl group. Substituents for the phenyl group include an alkyl group (for example, a methyl group, an ethyl group, etc.), an alkoxy group (for example, a methoxy group, an ethoxy group, etc.), an aryloxy group (for example, a phenoxy group, etc.), an alkoxycarbonyl group (for example, a methoxycarbonyl group, etc.), an acylamino group (for example, an acetylamino group, etc.), a carbamoyl group, an alkylcarbamoyl group (for example, a methylcarbamoyl group, an ethylcarbamoyl group, etc.), a dialkylcarbamoyl group (for example, a dimethylcarbamoyl group, etc.), an arylcarbamoyl group (for example, a phenylcarbamoyl group, etc.), an alkylsulfonyl group (for example, a methylsulfonyl group, etc.), an arylsulfonyl group (for example, a phenylsulfonyl group, etc.), an alkylsulfonamido group (for example, a methanesulfonamido group, etc.), an arylsulfonamido group (for example, a phenylsulfonamido group, etc.), a sulfamoyl group, an alkylsulfamoyl group (for example, an ethylsulfamoyl group, etc.), a dialkylsulfamoyl group (for example, a dimethylsulfamoyl group, etc.), an alkylthio group (for example, a methylthio group, etc.), an arylthio group (for example, a phenylthio group, etc.), a cyano group, a nitro group, a halogen atom (for example, fluorine, chlorine, bromine, etc.), and the like. When two or more substituents are present, they may be the same or different.

Particularly preferred substituents include a halogen atom, an alkyl group, an alkoxy group, an alkoxycarbonyl group and a cyano group. As Ar, those in which at least one of the ortho positions thereof is substituted with a halogen atom, an alkyl group or an alkoxy group are particularly useful.

Z represents a group which is directly bonded to the coupling position and is capable of being released upon the coupling reaction with an oxidation product of an aromatic primary amine developing agent. More specifically, Z represents hydrogen or a releasable group containing an oxygen atom, a nitrogen atom or a sulfur atom through which it is bonded to the coupling position. When Z represents the releasable group containing an oxygen atom, a nitrogen atom or a sulfur atom, these atoms are bonded to an alkyl group, an aryl group, a sulfonyl group, a sulfinyl group, a carbonyl group, a phosphoric acid group, a thiocarbonyl group, a heterocyclic group or a cyano group, and when Z represents the releasable group containing a nitrogen atom, it represents a releasable group which forms a 5-membered or 6-membered ring together with the nitrogen atom.

m represents 0 or 1, and n represents 0 or 1.

Examples of the non-color forming monomer which does not couple with the oxidation product of an aromatic primary amine developing agent include an ester, preferably a lower alkyl ester and an amide, derived from an acrylic acid, for example, an acrylic acid, an α-chloroacrylic acid, an α-alkylacrylic acid such as a methacrylic acid, for example, acrylamide, methacrylamide, t-butylacrylamide, methyl acrylate, ethyl acrylate, n-propyl acrylate, n-butyl acrylate, 2-ethylhexyl acrylate, n-hexyl acrylate, octyl methacrylate, lauryl methacrylate, methylene bisacrylamide, etc., a vinyl ester, for example, vinyl acetate, vinyl propionate, vinyl laurate, etc., acrylonitrile, methacrylonitrile, an aromatic vinyl compound, for example, styrene and a derivative thereof, for example, vinyl toluene, divinyl toluene, divinyl benzene, vinyl acetophenone, sulfo styrene, etc., itaconic acid, citraconic acid, crotonic acid, vinylidene chloride, a vinyl alkyl ether, for example, vinyl ethyl ether, an ester of maleic acid, N-vinyl-2-pyrrolidone, N-vinyl pyridine, 2- or 4-vinyl pyridine, etc.

Of these monomers, an ester of acrylic acid, an ester of methacrylic acid and an ester of maleic acid are particularly preferred.

Two or more comonomer compounds described above can be used together with. For example, a combination of n-butyl acrylate and divinyl benzene, styrene and methacrylic acid, n-butyl acrylate and methacrylic acid, etc., can be used.

The ethylenically unsaturated monomer which is used to copolymerize with the monomer coupler represented by the above-described general formula (II) can be selected so that the copolymer to be formed possesses good physical properties and/or chemical properties, for example, solubility, compatibility with a binder such as gelatin in a photographic colloid composition, flexibility, heat stability, etc., as well known in the field of polymer color couplers.

The magenta polymer coupler latex used in the present invention can be prepared by an emulsion polymerization method, as described above, or by dissolving a lipophilic polymer coupler obtained by polymerization of a monomer coupler in an organic solvent and then dispersing the solution in a latex form in an aqueous gelatin solution. With respect to the emulsion polymerization, the methods as described in U.S. Pat. Nos. 4,080,211 and 3,370,952 can be employed and with respect to the method in which a lipophilic polymer coupler is dispersed in a latex form in an aqueous gelatin solution, the method as described in U.S. Pat. No. 3,451,820 can be employed. These methods can be applied to preparation of homopolymers and preparation of copolymers. In the latter case, a non-color forming comonomer is preferably a liquid comonomer which may act, in the case of the emulsion polymerization, as a solvent for a monomer which is solid in normal state.

Free radical polymerization of an ethylenically unsaturated solid monomer is initiated with the addition to the monomer molecule of a free radical which is formed by thermal decomposition of a chemical initiator, an action of a reducing agent to an oxidative compound (a redox initiator) or a physical action with, for example, ultraviolet rays or other high energy radiations, high frequencies, etc.

Examples of the chemical initiators commonly used include a water-soluble initiator, for example, a persulfate (such as ammonium persulfate, potassium persulfate, etc.), hydrogen peroxide, 4,4'-azobis(4-cyanovaleric acid), etc., and a water-insoluble initiator, for example, azoisobutyronitrile, benzoyl peroxide, chlorobenzoyl peroxide, and other compounds. Examples of the redox initiators usually used include hydrogen peroxide-iron (II) salt, potassium persulfate-potassium hydrogensulfate, cerium salt-alcohol, etc. Specific examples and functions of the initiators are described in F. A. Bovey, *Emulsion Polymerization*, pages 59 to 93 (Interscience Publications Ind., New York (1955)).

The emulsifier used in the emulsion polymerization is a compound having surface activity. Preferred examples include soap, a sulfonate, a sulfate, a cationic compound, an amphoteric compound and a high molecular weight protective colloid. Specific examples and functions of the emulsifiers are described in *Belgische Chemische Industrie*, Vol. 28, pages 16 to 20 (1963).

The organic solvent which is used for dissolving a lipophilic polymer coupler when the lipophilic polymer coupler is dispersed in a latex form in an aqueous gelatin solution is removed from the mixture before coating of the dispersion solution. The solvent may also be removed by vaporization during drying of the dispersion solution coated, although this process is less preferable. With respect to removing the solvent, a method in which the solvent is removed by washing a gelatin noodle with water is used when the solvent is water-soluble to some extent, or a spray drying method, a vacuum purging method or a steam purging method can be employed for removing the solvent.

Examples of the organic solvents which can be removed include, for example, an ester (for example, a lower alkyl ester, etc.), a lower alkyl ether, ketone, halogenated hydrocarbon (for example, methylene chloride, trichloroethylene, a fluorinated hydrocarbon, etc.), an alcohol (for example, an alcohol between n-butyl alcohol and octyl alcohol, etc.), and a mixture thereof.

Any type of dispersing agent can be used in the dispersion of the lipophilic polymer coupler. Ionic surface active agents, and particularly anionic surface active agents are preferred. Amphoteric surface active agents such as C-cetyl betaine, an N-alkylaminopropionate, N-alkyliminodipropionate etc., can also be used.

It is desirable if a ratio of the color forming portion in the polymer coupler latex is from 5 to 80% by weight. In this case, an equivalent molecular weight, that is, a gram number of the polymer containing 1 mol of a coupler monomer is preferably from about 250 to 3,000, but it is not limited thereto.

Specific examples of the coupler monomers which are suitable for use in the production of the magenta polymer coupler latex are described, for example, in U.S. Pat. No. 3,163,625, British Pat. No. 1,247,688, West German Patent Application (OLS) No. 2,725,591, U.S. Pat. No. 3,926,436, Japanese Patent Application No. 171544/80 (corresponding to U.S. Patent Application filed on Dec. 7, 1981), etc.

Particularly preferred specific examples of the coupler monomers used in the present invention are set forth below, but the present invention is not to be construed as being limited thereto.

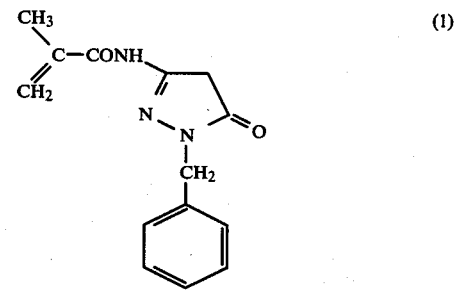

(1)

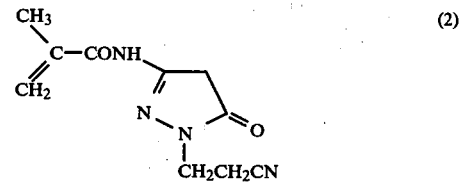

(2)

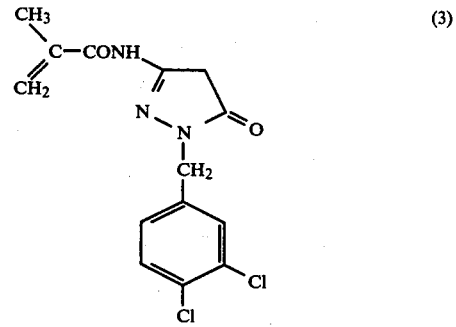

(3)

-continued
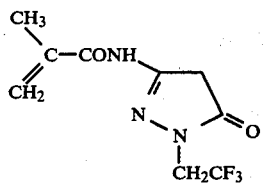 (4)
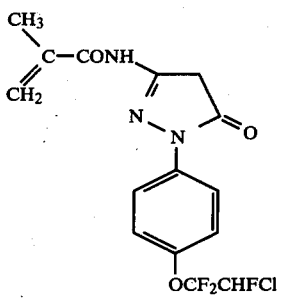 (5)
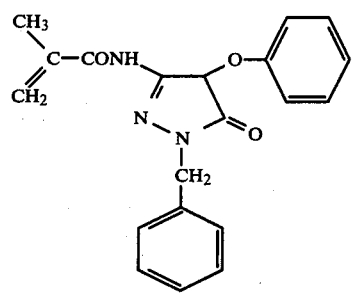 (6)
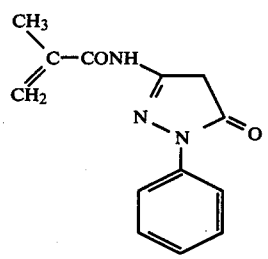 (7)
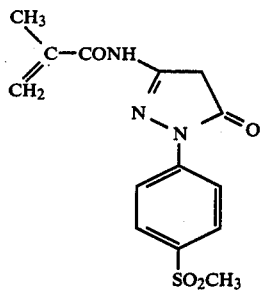 (8)
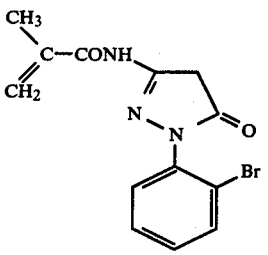 (9)
-continued
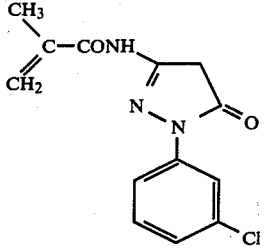 (10)
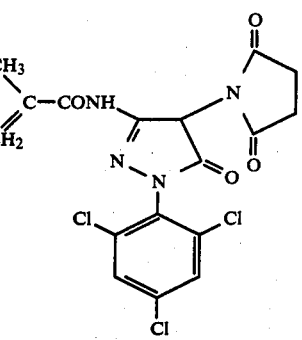 (11)
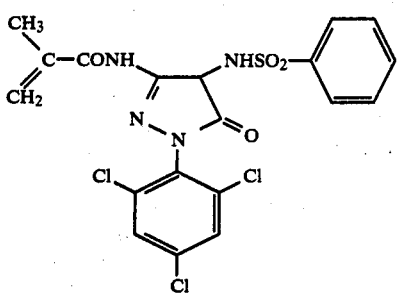 (12)
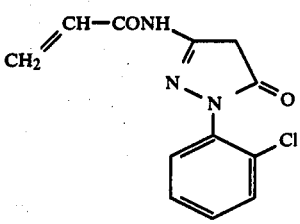 (13)

-continued
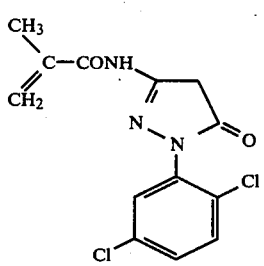 (16)
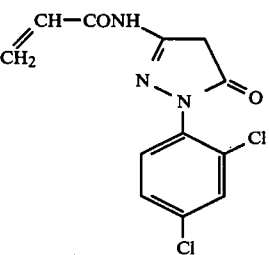 (17)
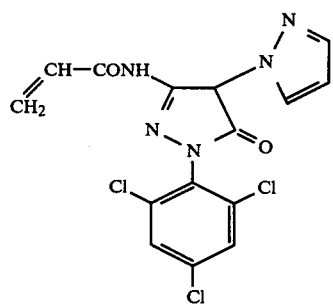 (18)
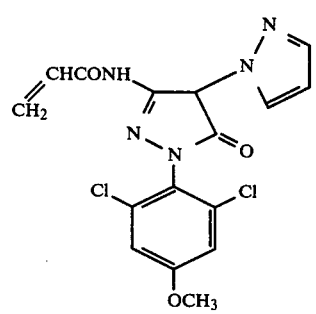 (19)
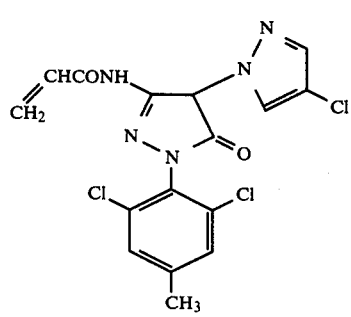 (20)
-continued
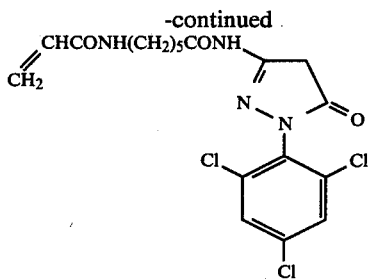 (21)
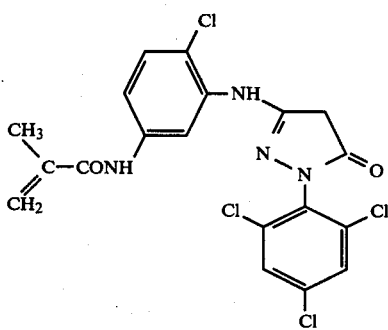 (22)
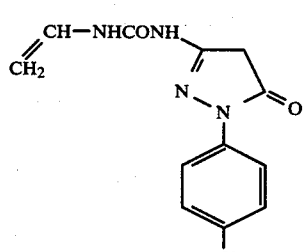 (23)
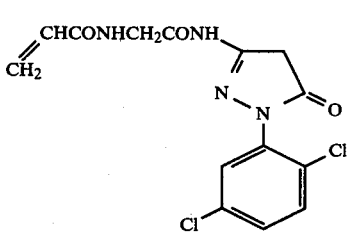 (24)
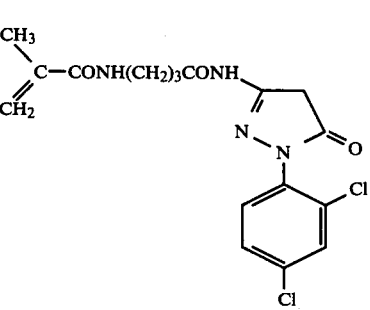 (25)
Specific examples for the preparation of the magenta polymer coupler latex are set forth below.
PREPARATION EXAMPLE 1
Copolymer latex of 1-phenyl-3-methacrylamido-2-pyrazolin-5-one [Coupler Monomer (7)] and n-butyl acrylate [Polymer Coupler latex (A)]
180 ml of an aqueous solution containing 3.5 g of sodium salt of oleyl methyl tauride dissolved therein was stirred and heated to 95° C. while gradually introducing nitrogen gas through the solution. To the mixture was added 20 ml of an aqueous solution containing 240 mg of potassium persulfate dissolved therein. 60 g n-butyl acrylate and 10 g of 1-phenyl-3-methacrylamido-2-pyrazolin-5-one [Coupler Monomer (7)] were dissolved by heating and the resulting solution was added to the above-described aqueous solution at an interval of about 30 seconds while preventing the deposition of crystals. After the completion of the addition, the mixture was heated at from 90° C. to 95° C. with stirring for 45 minutes, and then to the mixture was added 10 ml of an aqueous solution containing 120 mg of potassium persulfate dissolved therein. After further being reacted for 1 hour, the unreacted n-butyl acrylate was distilled off as an azeotropic mixture with water. The latex thus-formed was cooled and filtered. The concentration of the polymer in the latex was 27.6% and it was found that the copolymer prepared contained 18.1% of 1-phenyl-3-methacrylamido-2-pyrazolin-5-one as the result of nitrogen analysis.

PREPARATION EXAMPLE 2

Copolymer latex of 1-(2,5-dichlorophenyl)-3-methacrylamido-5-oxo-2-pyrazoline [Coupler Monomer (16)] and n-butyl acrylate [Polymer Coupler Latex (B)]

2 liters of an aqueous solution containing 2 g of sodium salt of oleyl methyl tauride dissolved therein was stirred and heated to 95° C. while gradually introducing nitrogen gas through the solution. To the mixture was added 40 ml of an aqueous solution containing 280 mg of potassium persulfate dissolved therein. Then, 20 g of n-butyl acrylate and 20 g of Coupler Monomer (16) were dissolved by heating in 400 ml ethanol. The resulting solution was added to the above-described aqueous solution at an interval of about 30 seconds while preventing the deposition of crystals. After the completion of the addition, the mixture was heated at from 85° C. to 95° C. with stirring for 45 minutes, and then to the mixture was added 40 ml of an aqueous solution containing 120 mg of potassium persulfate dissolved therein. After further being reacted for 1 hour, the unreacted n-butyl acrylate was distilled off as an azeotropic mixture with water. The latex thus-formed was cooled, and the pH was adjusted to 6.0 with a 1 N sodium hydroxide solution and filtered. The concentration of the polymer in the latex was 7.63% and it was found that the copolymer prepared contained 48.3% of 1-(2,5-dichlorophenyl)-3-methacrylamido-5-oxo-2-pyrazoline as the result of nitrogen analysis.

PREPARATION EXAMPLE 3

Copolymer latex of 1-(2,4,6-trichlorophenyl)-3-acrylamido-5-oxo-2-pyrazoline [Coupler Monomer (18)] and n-ethyl acrylate [Polymer Coupler Latex (C)]

2 liters of an aqueous solution containing 2 g of sodium salt of oleyl methyl tauride dissolved therein was stirred and heated to 95° C. while gradually introducing nitrogen gas through the solution. To the mixture was added 40 ml of an aqueous solution containing 280 mg of potassium persulfate dissolved therein. Then, 20 g of n-ethyl acrylate and 20 g of Coupler Monomer (18) were dissolved by heating in 400 ml of methanol and the resulting solution was added to the above-described aqueous solution at an interval of about 30 seconds while preventing the deposition of crystals. After the completion of the addition, the mixture was heated at from 85° C. to 95° C. with stirring for 45 minutes, and then to the mixture was added 40 ml of an aqueous solution containing 120 mg of potassium persulfate dissolved therein. After being further reacted for 1 hour, the unreacted n-ethyl acrylate was distilled off as an azeotropic mixture with water. The latex thus-formed was cooled, and the pH was adjusted to 6.0 with a 1 N sodium hydroxide solution and filtered. The concentration of the polymer in the latex was 8.53% and it was found that the copolymer prepared contained 47.3% of 1-(2,4,6-trichlorophenyl)-3-acrylamido-5-oxo-2-pyrazoline as the result of nitrogen analysis.

PREPARATION EXAMPLE 4

Copolymer latex of 1-(2,4,6-trichlorophenyl)-3-acrylamido-4-pyrazolyl-5-oxo-2-pyrazoline [Coupler Monomer (11)] and n-butyl acrylate [Polymer Coupler Latex (D)]

2 liters of an aqueous solution containing 2 g of sodium salt of oleyl methyl tauride dissolved therein was stirred and heated to 95° C. while gradually introducing nitrogen gas through the solution. To the mixture was added 40 ml of an aqueous solution containing 280 mg of potassium persulfate dissolved therein. Then 20 g of n-butyl acrylate and 20 g of Coupler Monomer (11) were dissolved by heating in 400 ml of ethanol and the resulting solution was added to the above-described aqueous solution at an interval of about 30 seconds while preventing the deposition of crystals. After the completion of the addition, the mixture was heated at from 85° C. to 95° C. with stirring for 45 minutes, and then to the mixture was added 40 ml of an aqueous solution containing 120 mg of potassium persulfate dissolved therein. After being reacted for 1 hour, the unreacted n-butyl acrylate was distilled off as an azeotropic mixture with water. The latex thus-formed was cooled, and the pH was adjusted to 6.0 with a 1 N sodium hydroxide solution and filtered. The concentration of the polymer in the latex was 10.5% and it was found that the copolymer synthesized contained 45.7% of 1-(2,4,6-trichlorophenyl)-3-acrylamido-4-pyrazolyl-5-oxo-2-pyrazoline as the result of nitrogen analysis.

PREPARATION EXAMPLE 5

Preparation of Lipophilic Polymer Coupler 1

To a mixture of 20 g of Coupler Monomer (10), 20 g of ethyl acrylate and 150 ml of tertiary butanol was added 350 mg of azobisisobutyronitrile dissolved in 10 ml of tertiary butanol while refluxing by heating with stirring and the mixture was refluxed for about 1 hour. The resulting mixture was then poured into 2 liters of ice water and the solid thus deposited was collected by filtration and thoroughly washed with water. By drying the product, 35.2 g of the lipophilic polymer coupler was obtained.

It was found that the lipophilic polymer coupler contained 51.3% of Coupler Monomer (10) in the copolymer prepared as the result of nitrogen analysis.

Preparation of Polymer Coupler Latex (E)

Two solutions (a) and (b) were prepared in the following manner.

Solution (a): 300 g of a 5% by weight aqueous solution of bone gelatin (pH of 5.6 at 35° C.) was heated to 32°

C. to which was added 12 ml of a 10% by weight aqueous solution of sodium lauryl sulfate.

Solution (b): 20 g of the lipophilic polymer coupler was dissolved in 60 g of ethyl acetate at 38° C.

Solution (b) was put into a mixer with an explosion preventing equipment while stirring at high speed and thereto was rapidly added Solution (a). After stirring for 1 minute, the mixer was stopped and ethyl acetate was removed by distillation under a reduced pressure. Thus the lipophilic polymer coupler was dispersed in a diluted gelatin solution to prepare Polymer Coupler Latex (E).

Preparation of Polymer Coupler Latex (F)

Polymer Coupler Latex (F) was prepared in the same procedure as in the above described Polymer Coupler Latex (E).

PREPARATION EXAMPLES 7 TO 26

Using the above described coupler monomers, the magenta polymer coupler latexes described below were prepared in the same manner as described for the copolymers in Preparation Examples 1 to 4 (Preparation Method I) and in Preparation Examples 5 to 6 (Preparation Method II).

| | | Preparation Method I | | | | |
|---|---|---|---|---|---|---|
| Preparation Example | Polymer Coupler Latex | Coupler Monomer | Amount (g) | Comonomer(*1) | Amount (g) | Coupler Monomer Unit in Polymer (%) |
| 7 | (G) | (2) | 10 | BA | 10 | 51.3 |
| 8 | (H) | (4) | 10 | EA | 10 | 49.6 |
| 9 | (I) | (8) | 10 | BA | 10 | 47.3 |
| 10 | (J) | (8) | 10 | BA | 40 | 20.4 |
| 11 | (K) | (10) | 10 | MA | 10 | 48.9 |
| 12 | (L) | (11) | 10 | EA | 20 | 35.1 |
| 13 | (M) | (15) | 10 | BMA | 10 | 50.4 |
| 14 | (N) | (16) | 10 | EA | 10 | 53.2 |
| 15 | (O) | (16) | 10 | MMA | 10 | 50.9 |
| 16 | (P) | (17) | 10 | BA | 10 | 48.5 |
| 17 | (Q) | (18) | 10 | BA | 5 | 67.2 |
| 18 | (R) | (19) | 10 | MA | 10 | 50.4 |
| 19 | (S) | (23) | 10 | MMA | 40 | 20.1 |
| 20 | (T) | (24) | 10 | BA | 10 | 46.3 |

| | | Preparation Method II | | | | |
|---|---|---|---|---|---|---|
| Preparation Example | Polymer Coupler Latex | Coupler Monomer | Amount (g) | Comonomer(*1) | Amount (g) (%) | Coupler Monomer Unit in Polymer |
| 21 | (U) | (7) | 10 | EA | 40 | 21.3 |
| 22 | (V) | (9) | 10 | MA | 40 | 20.5 |
| 23 | (W) | (11) | 10 | EA | 20 | 38.3 |
| 24 | (X) | (16) | 10 | EA | 10 | 55.3 |
| 25 | (Y) | (17) | 10 | BA | 20 | 36.1 |
| 26 | (Z) | (21) | 10 | MA | 10 | 51.2 |

(*1)
BA: Butyl Acrylate
EA: Ethyl Acrylate
MA: Methyl Acrylate
BMA: Butyl Methacrylate
MMA: Methyl Methacrylate

PREPARATION EXAMPLE 6

Preparation of Lipophilic Polymer Coupler 2

To a mixture of 20 g of Coupler Monomer (16), 20 g of n-butyl acrylate and 150 ml of dioxane was added 350 mg of azobisisobutyronitrile dissolved in 10 ml of dioxane while heating at 60° C. with stirring and the mixture was reacted for about 5 hours. The resulting mixture was then poured into 2 liters of ice water and the solid thus deposited was collected by filtration and thoroughly washed with water. By drying the product, 38.4 g of the lipophilic polymer coupler was obtained. It was found that the lipophilic polymer coupler contained 55.1% of Coupler Monomer (16) in the copolymer prepared as the result of nitrogen analysis.

Two or more kinds of the magenta polymer coupler latexes described above can be incorporated into the same layer, or the same latex compound can also be added to two or more layers in order to satisfy the characteristics required of the photographic light-sensitive material. In general, the polymer coupler latex is coated in a ratio of $1 \times 10^{-4}$ mol/m$^2$ to $5 \times 10^{-3}$ mol/m$^2$, and preferably $3 \times 10^{-4}$ mol/m$^2$ to $2 \times 10^{-3}$ mol/m$^2$ based on the coupler monomer.

Further, a dispersion which is prepared by dispersing a hydrophobic magenta color forming coupler, for example, a magenta coupler, as described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, etc., in a hydrophilic colloid in a manner as described, for example, in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the magenta polymer coupler latex according to the present invention in a manner as described in Japanese Patent Application (OPI) No. 39853/76, etc., and the resulting latex can be used. The above-described hydrophobic magenta coupler is loaded into the magenta polymer coupler latex in a manner as described in Japanese Patent Application (OPI) Nos. 59942/76 and 32552/79, U.S. Pat. No. 4,199,363, etc., and the resulting latex can be used. The term "load" used herein refers to the state in which a hydrophobic magenta coupler is incorporated into the interior of a magenta polymer coupler latex, or a state in which a hydrophobic magenta coupler is deposited on the surface of a magenta polymer coupler latex. However, it has not been accurately understood in what kind of mechanism the load occurs.

In order to satisfy the characteristics required of the photographic light-sensitive material, a dispersion which is prepared by dispersing a development inhibitor releasing (DIR) coupler as described, for example, in U.S. Pat. Nos. 3,148,062, 3,227,554, 3,733,201, 3,617,291, 3,703,375, 3,615,506, 3,265,506, 3,620,745, 3,632,345, 3,869,291, 3,642,485, 3,770,436 and 3,808,945, British Pat. Nos. 1,201,110 and 1,236,767, etc., in a hydrophilic colloid in a manner as described in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the magenta polymer coupler latex according to the present invention in a manner as described in Japanese Patent Application (OPI) No. 39853/76, etc., and the resulting latex can then be used. The above-described DIR coupler is loaded into the magenta polymer coupler latex in a manner as described in Japanese Patent Application (OPI) Nos. 59942/76 and 32552/79, U.S. Pat. No. 4,199,363, etc., and the resulting latex can then be used.

Furthermore, the magenta polymer coupler latex according to the present invention can be used together with a DIR compound as described, for example, in West German Patent Application (OLS) Nos. 2,529,350, 2,448,063 and 2,610,546, U.S. Pat. Nos. 3,928,041, 3,958,993, 3,961,959, 4,049,455, 4,052,213, 3,379,529, 3,043,690, 3,364,022, 3,297,445 and 3,287,129, etc.

Moreover, the magenta polymer coupler latex according to the present invention can be used in combination with a colored magenta coupler as described, for example, in U.S. Pat. No. 2,449,966, West German Pat. No. 2,024,186, Japanese Patent Application (OPI) Nos. 123625/74, 131448/74 and 42121/77, etc., a competitive coupler as described, for example, in U.S. Pat. Nos. 3,876,428, 3,580,722, 2,998,314, 2,808,329, 2,742,832 and 2,689,793, etc., or the like.

The color photographic light-sensitive material produced according to the present invention can also contain a conventionally well known coupler(s) other than a magenta color forming coupler. A non-diffusible coupler which contains a hydrophobic group, called a ballast group, in the molecule thereof is preferred as a coupler. A coupler can have either a 4-equivalent or a 2-equivalent property with respect to the silver ion. In addition, a colored coupler providing a color correction effect, or a coupler which releases a development inhibitor upon development can also be present therein. Furthermore, a coupler which provides a colorless product upon coupling can be employed.

A known open chain ketomethylene type coupler can be used as a yellow color forming coupler. Of these couplers, benzoyl acetanilide type and pivaloyl acetanilide type compounds are especially effective. Specific examples of yellow color forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76 and 87650/75, etc.

A phenol type compound, a naphthol type compound, etc., can be employed as a cyan color forming coupler. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 73050/80, etc.

Two or more kinds of the couplers described above can be incorporated into the same layer, or the same coupler compound can also be present in two or more layers.

A known method described, for example, in U.S. Pat. No. 2,322,027, can be used to incorporate the couplers described above into a silver halide emulsion layer. The coupler is dispersed in a hydrophilic colloid and then mixed with a silver halide emulsion. When a coupler having an acid group such as a carboxylic acid group, a sulfonic acid group, etc., is used, it can be incorporated into a hydrophilic colloid as an alkaline aqueous solution thereof.

The silver halide emulsions which can be used in the present invention are those wherein silver chloride, silver bromide, or a mixed silver halide such as silver chlorobromide, silver iodobromide, or silver chloroiodobromide is finely dispersed in a hydrophilic polymer such as gelatin. The silver halide can be chosen depending on the intended use of the photographic light-sensitive material from dispersions having a uniform grain size or those having a wide grain size distribution or from dispersions having an average grain size of from about 0.1 micron to 3 microns. These silver halide emulsions can be prepared, for example, by a single jet method, by a double jet method or a controlled double jet method, and by a ripening method such as an ammonia method, a neutral method, or an acid method. Also, these silver halide emulsions can be subjected to chemical sensitization such as a sulfur sensitization, a gold sensitization, a reduction sensitization, etc., and can contain a speed increasing agent such as a polyoxyethylene compound, an onium compound, etc. Further, a silver halide emulsion of the type wherein latent images are predominantly formed on the surface of the grains or of the type where latent images are predominantly formed inside the grains can be used in the present invention. Also, two or more kinds of silver halide photographic emulsions prepared separately and then mixed can be employed.

Examples of useful hydrophilic high molecular weight substances which make up the photographic light-sensitive layer of the present invention include proteins such gelatin, etc., high molecular weight non-electrolytes such as polyvinyl alcohol, polyvinyl pyrrolidone, polyacrylamide, etc., acidic polymers such as an alginate, a polyacrylic acid salt, etc., high molecular weight ampholites such as a polyacrylamide treated by the Hoffman rearrangement reaction, copolymers of acrylic acid and N-vinylimidazole. Furthermore, a hydrophobic polymer dispersion such as a latex of polybutyl acrylate, etc., can be included in the continuous phase of such a hydrophilic high molecular weight substance.

The silver halide emulsion used in the present invention can be chemically sensitized using conventional methods. Examples of suitable chemical sensitizers include, for example, gold compounds such as chloroaurates and gold trichloride as described in U.S. Pat. Nos. 2,399,083, 2,540,085, 2,597,856, and 2,597,915; salts of a noble metal, such as platinum, palladium, iridium, rhodium and ruthernium, as described in U.S. Pat. Nos. 2,448,060, 2,540,086, 2,566,245, 2,566,263 and 2,598,079; sulfur compounds capable of forming silver sulfide by reacting with a silver salt, such as those described in U.S. Pat. Nos. 1,574,944, 2,410,689, 3,189,458 and 3,501,313; stannous salts amines, and other reducing compounds such as those described in U.S. Pat. Nos. 2,487,850, 2,518,698, 2,521,925, 2,521,926, 2,694,637, 2,983,610 and 3,201,254 and the like.

Various compounds can be added to the photographic emulsions used in the present invention in order to prevent a reduction of the sensitivity or a formation of fog during preparation, storage, or processing of the photographic light-sensitive material. A wide variety of such compounds are known, such as heterocyclic compounds, mercury-containing compounds, mercapto compounds or metal salts, including 4-hydroxy-6-methyl-1,3,3a,7-tetraazaindene, 3-methylbenzothiazole and 1-phenyl-5-mercaptotetrazole. Other examples of such compounds which can be used are described in U.S. Pat. Nos. 1,758,576, 2,110,178, 2,131,038, 2,173,628, 2,697,040, 2,304,962, 2,324,123, 2,394,198, 2,444,605, 2,444,606, 2,444,607, 2,444,608, 2,566,245, 2,694,716, 2,697,099, 2,708,162, 2,728,663, 2,728,664, 2,728,665, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668 and 3,622,339, British Pat. Nos. 893,428, 403,789, 1,173,609 and 1,200,188, as well as in K. Mees, *The Theory of the Photographic Process*, 3rd Ed. (1966) and the literature references cited therein.

The photographic emulsion used in the present invention can also contain one or more surface active agents. These surface active agents are commonly used as a coating aid. However, in some cases they are used for the purpose of emulsified dispersion, sensitization, static preventing, adhesive preventing, etc.

The surface active agents can be classified into various groups, as follows: natural surface active agents such as saponin; nonionic surface active agents such as alkylene oxides, glycerols and glycidols; cationic surface active agents such as higher alkylamines, quaternary ammonium salts, heterocyclic compounds such as pyridine and the like, phosphoniums or sulfoniums; anionic surface active agents containing an acid group such as a carboxylic acid group, a sulfonic acid group, a phosphoric acid group, a sulfuric acid ester group, or phosphoric acid ester group; amphoteric surface active agents such as aminoacids, aminosulfonic acids, amino-alcohol sulfuric acid esters or amino-alcohol phosphoric acid esters. Some examples of those surface active agents which can be used are described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974, West German Patent Application (OLS) No. 1,942,665, British Pat. Nos. 1,077,317 and 1,198,450, as well as Ryohei Oda et al., *Kaimenkasseizai no Gosei to sono Oyo (Synthesis and Application of Surface Active Agents)*, Maki Shoten (1964), A. W. Perry, *Surface Active Agents*, Interscience Publications, Inc. (1958) and J. P. Sisley, *Encyclopedia of Surface Active Agents*, Vol. II, Chemical Publishing Co. (1964).

The photographic emulsions can be spectrally sensitized, or supersensitized, using a cyano-type dye, such as a cyanine, merocyanine, carbocyanine, etc., individually, in combinations, or in combination with a styryl dye.

These spectral sensitization techniques are well known, and are described, for example, in U.S. Pat. Nos. 2,688,545, 2,912,329, 3,397,060, 3,615,635 and 3,628,964, British Pat. Nos. 1,195,302, 1,242,588 and 1,293,862, West German Patent Application (OLS) Nos. 2,030,326 and 2,121,780, Japanese Patent Publication Nos. 4936/68 and 14030/69, etc. The sensitizers can be selected as desired depending on the wavelength range to be sensitized or the purposes and use of the photographic materials to be sensitized.

The hydrophilic colloid layer, and in particular a gelatin layer in the photographic light-sensitive material used in the present invention, can be hardened using various kinds of cross-linking agents. For instance, an inorganic compound such as a chromium salt and a zirconium salt, or an aldehyde type cross-linking agent such as mucochloric acid, or 2-phenoxy-3-chloromalealdehydic acid as described in Japanese Patent Publication No. 1872/71 can be effectively used in the present invention, but non-aldehyde type cross-linking agents such as compounds having plural epoxy rings as described in Japanese Patent Publication No. 7133/59, the poly(1-aziridinyl) compounds as described in Japanese Patent publication No. 8790/62, the active halogen compounds as described in U.S. Pat. Nos. 3,362,827 and 3,325,287 and the vinyl sulfone compounds as described in U.S. Pat. Nos. 2,994,611 and 3,582,322, Belgian Pat. No. 686,440, etc., are particularly suitable for use in the photographic light-sensitive material of the present invention.

The silver halide photographic emulsion of the present invention is suitably applied to a support. Illustrative supports include rigid materials such as glass, metal and ceramics, and flexible materials and the type of support chosen depends on the end-use objects. Typical examples of flexible supports include a cellulose nitrate film, a cellulose acetate film, a polyvinyl acetal film, a polystyrene film, a polyethylene terephthalate film, a polycarbonate film and a laminate thereof, a baryta coated paper, a paper coated with an α-olefin polymer, such as polyethylene, polypropylene and an ethylene-butene copolymer, a plastic film having a roughened surface as described in Japanese Patent Publication No.

19068/72, and the like. Depending upon the end-use objects of the photographic light-sensitive material, the support can be transparent, colored by adding a dye or pigment, opaque by adding, for example, titanium white, or light-shielding by adding, for example, carbon black.

The layer of the photographic light-sensitive material can be coated on a support using various coating methods, including a dip coating method, an air-knife coating method, a curtain coating method, an extrusion coating method using a hopper as described in U.S. Pat. No. 2,681,294. Also, two or more layers can be coated simultaneously, using methods as described in U.S. Pat. Nos. 2,761,791, 3,508,947, 2,941,898, 3,526,528, etc.

The present invention is applicable to not only the so-called multilayer type photographic light-sensitive material comprising a support having superimposed thereon emulsion layers, each of which is sensitive to radiation of a substantially different wavelength region and forms color images of a substantially different hue, but also the so-called mixed-packet type photographic light-sensitive material comprising a support having coated thereon a layer containing packets which are sensitive to radiation of substantially different wavelength regions and form color images of a substantially different hue. The present invention can be applied to a color negative film, a color positive film, a color reversal film, a color printing paper, a color reversal printing paper, and the like.

The color photographic light-sensitive material of the present invention is, after exposure, subjected to a development processing to form dye images. Development processing includes basically a color development step, a bleaching step and a fixing step. Each step can be carried out individually or two or more steps can be combined as one step where a processing solution having two or more functions is used. Also, each step can be separated into two or more steps. The development processing can further include a pre-hardening step, a neutralization step, a first development (black-and-white development) step, a stabilizing step, a water washing step, and the like, if desired. The temperature of processing can be varied depending on the photographic light-sensitive material, the processing method, and the like. In general, the processing steps are carried out at a temperature from 18° C. to 60° C. These steps need not necessarily be conducted at the same temperature.

A color developer solution is an alkaline solution having a pH of more than 8, preferably from 9 to 12, and containing, as a developing agent, a compound whose oxidation product is capable of forming a colored compound when reacted with a color forming agent, i.e., a color coupler. The developing agent described above includes a compound capable of developing an exposed silver halide and having a primary amino group on an aromatic ring, and a precursor which forms such compound. Typical examples of preferred developing agents are, for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-ethoxyethylaniline, 4-amino-3-methoxy-N-ethyl-N-β-methoxyethylaniline, 4-amino-3-β-methanesulfonamidoethyl-N,N-diethylaniline, and the salts thereof (for example, the sulfates, the hydrochlorides, the sulfites, the p-toluene sulfonates, and the like). Other developing agents such as those described in U.S. Pat. Nos. 2,193,015 and 2,592,364, Japanese Patent Application (OPI) No. 64933/73, L. F. A. Mason, *Photographic Processing Chemistry*, pages 226–229, Focal Press, London (1966), etc., can be used. Also, a 3-pyrazolidone can be used together with these developing agents.

The color developer solution can optionally contain various additives, Typical examples of such additives include alkaline agents (for example, alkali metal or ammonium hydroxide, carbonates or phosphates); pH-adjusting agents or buffers (for example, weak acids such as acetic acid, boric acid, etc., weak bases, or salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides; alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing such as those described in U.S. Pat. Nos. 3,113,864, 3,342,596, 3,295,976, 3,615,522 and 3,597,199; thiosulfonyl compounds such as those described in British Pat. No. 972,211; phenazine-N-oxides such as those described in Japanese Patent Publication No. 41675/71; those described in *Kagaku Shashin Binran (Manual of Scientific Photography)*, Vol. 11, page 29–47, and the like); stain or sludge preventing agents such as those described in U.S. Pat. Nos. 3,161,513 and 3,161,514, and British Pat. Nos. 1,030,442, 1,144,481 and 1,251,558; interlayer-effect accelerators disclosed in U.S. Pat. No. 3,536,487; preservatives (for example, sulfites, bisulfites, hydroxyamine hydrochloride, formsulfite, alkanolaminesulfite adducts, etc.) and the like.

The color photographic light-sensitive material of the present invention can be treated with various solutions prior to color development.

In the case of color reversal films, treatment with a first development solution is also carried out prior to color development. As the first development solution, an alkaline aqueous solution containing at least one developing agent, such as hydroquinone, 1-phenyl-3-pyrazolidone, N-methyl-p-aminophenol and the like can be employed. The solution can also contain inorganic salts such as sodium sulfate; pH-adjusting agents or buffers such as borax, boric acid, sodium hydroxide and sodium carbonate; development fog inhibitors such as alkali metal halides (such as potassium bromide, etc.), and the like.

The additives illustrated above and the amounts thereof employed are well known in the color processing field.

After color development, the color photographic materials are usually bleached and fixed. The process can be effected in a blix bath which combines the bleaching and fixing steps. Various compounds can be used as a bleaching agent, for example, ferricyanides, dichromates; water-soluble iron (II) salts, water-soluble cobalt (III) salts; water-soluble copper (II) salts; water-soluble quinones; nitrosophenols; complex salts of a polyvalent cation such as iron (III), cobalt (III), copper (II), etc., and an organic acid, for example, metal complex of an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and copper complex salt of 2,6-dipicolinic acid; peracids such as alkylperacids, persulfates, permanganates and hydrogen peroxide; hypochlorites; chlorine; bromine; bleaching powder; and the like. These can be suitably used, individually or in combination. To the bleaching solution, bleaching accelerators such as those described in U.S. Pat. Nos. 3,042,520 and 3,241,966, Japanese Patent Publication Nos. 8506/70 and 8836/70 and various other additives can be added.

Any known fixing solution can be used for fixing the photographic materials of the present invention. That is, ammonium, sodium, or potassium thiosulfate can be used as a fixing agent at a concentration of about 50 to about 200 g/liter. Fixing solutions can further contain stabilizers such as sulfites and metabisulfites; hardeners such as potassium alum; pH buffers such as acetates and borates, and the like. The fixing solution generally has a pH of more than 3.

Bleaching baths, fixing baths and blixing baths as described, for example, in U.S. Pat. No. 3,582,322, Japanese Patent Application (OPI) No. 101934/73, West German Pat. No. 1,051,117 can also be employed.

The present invention will be explained in greater detail with reference to the following examples, but the present invention should not be construed as being limited thereto.

EXAMPLE 1

A mixture compound of 8 g of each of the compounds according to the present invention and the comparative compounds as shown in Table 1 below, 10 ml of tricresyl phosphate and 24 ml of ethyl acetate was dissolved by heating on a steam bath. The solution was added to 100 ml of an aqueous solution containing 10 g of gelatin and 0.5 g of sodium dodecylbenzenesulfonate. The resulting mixture was then stirred using a homogenizer to prepare a dispersion.

36.5 g of each of the dispersion, 200 ml of Polymer Coupler Latex (A) prepared by Preparation Example 1 and 100 ml of a 10% aqueous gelatin solution were mixed with 100 g of a silver halide emulsion containing $5.6 \times 10^{-2}$ mol of silver chlorobromide (silver chloride: 50 mol%) and 10 g of gelatin. To the mixture was added 8 ml of a 4% acetone solution of 2-hydroxy-4,6-dichloro-s-triazine sodium salt (per 100 g of the emulsion). After adjusting the pH to 6.5, the emulsion was coated on a cellulose triacetate film support to prepare Samples 1 to 10.

Sample 11 was prepared in the same manner as described above except that a dispersion containing a color fading preventing agent was not added and 133 g of a 10% aqueous gelatin solution was added.

These films were exposed stepwise for sensitometry and the subjected to the following color development processing.

| Color Development Processing Steps | | |
| --- | --- | --- |
| 1. Color Development | 33° C. | 3 min 30 sec |
| 2. Blixing | 33° C. | 1 min 30 sec |
| 3. Washing with Water | 30° C. | 2 min |

The composition of each processing solution used in the color development processing was as follows.

| Color Developer Solution | | |
| --- | --- | --- |
| Potassium Carbonate | 30 | g |
| Sodium Sulfite | 2 | g |
| Hydroxylamine (sulfate) | 2 | g |
| Potassium Bromide | 0.5 | g |
| Benzyl Alcohol | 15 | ml |
| Diethylene Glycol | 10 | ml |
| 4-(N—Ethyl-N—β-methanesulfonamido-ethyl)amino-2-methylaniline Sesquisulfate | 5 | g |
| Water to make | 1 | liter |
| | (pH 10.2) | |
| Blixing Solution | | |
| Ethylenediaminetetraacetic Acid Ferric Salt | 45 | g |
| Sodium Sulfite | 10 | g |
| Ammonium Thiosulfate (60 wt % aq. soln.) | 100 | ml |
| Sodium Ethylenediaminetetraacetate | 5 | g |
| Water to make | 1 | liter |
| | (pH 6.9) | |

Each of Samples 1 to 11 thus-processed was subjected to a fading test for 2 weeks using a day light type fluorescent lamp having an illumination of about 30,000 lux equipped with a filter capable of absorbing substantially all ultraviolet lights having a wavelength of 400 mµ or less. The color image fastness and the formation of yellow stain in a low density portion (fogged unexposed portion) were determined. The color image fastness was evaluated by calculating a rate of color density decrease (%) after the above described fading test at an area having an initial density (green light) of 1.0 and 2.0. Also, the yellow stain was evaluated by an optical density value measured with blue light after the above described fading test. The results thus obtained are shown in Table 1 below.

TABLE 1

| Sample | Color Fading Preventing Agent | Color Image Fastness | | Stain | Remarks |
| --- | --- | --- | --- | --- | --- |
| | | $D_{1.0}$ | $D_{2.0}$ | | |
| 1 | Compound (1) | 11 | 7 | 0.12 | Present Invention |
| 2 | Compound (8) | 8 | 6 | 0.10 | Present Invention |
| 3 | Compound (9) | 10 | 6 | 0.11 | Present Invention |
| 4 | Compound (15) | 12 | 7 | 0.12 | Present Invention |
| 5 | Comparative Compound (a) | 31 | 23 | 0.18 | Comparison |
| 6 | Comparative Compound (b) | 29 | 21 | 0.17 | Comparison |
| 7 | Comparative Compound (c) | 30 | 23 | 0.19 | Comparison |
| 8 | Comparative Compound (d) | 29 | 22 | 0.18 | Comparison |
| 9 | Comparative Compound (e) | 24 | 16 | 0.15 | Comparison |
| 10 | Comparative Compound (f) | 26 | 18 | 0.19 | Comparison |
| 11 | — | 32 | 24 | 0.20 | Comparison |

Comparative Compound (a)

-continued

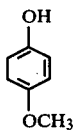
A compound described in British Patent 1,347,556

Comparative Compound (b)
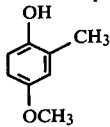
A compound described in British Patent 1,347,556

Comparative Compound (c)
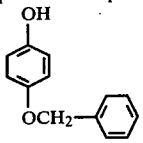
A compound described in British Patent 1,347,556

Comparative Compound (d)
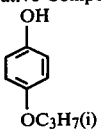
A compound described in British Patent 1,347,556

Comparative Compound (e)
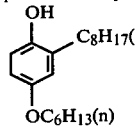
A compound described in British Patent 1,347,556 and Japanese Patent Application (OPI) No. 14023/76

Comparative Compound (f)
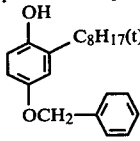
A compound described in Japanese Patent Application (OPI) No. 14023/76

From the results shown in Table 1 above, it is apparent that the p-alkoxyphenolic compounds in which tertiary alkyl groups are present at both the 2-position and 5-position are exceptionally effected for improving the fastness of color image to light and preventing the formation of yellow stain.

EXAMPLE 2

Samples 12 and 13 were prepared in the same manner as described in Example 1 using 63.9 ml of an aqueous solution containing $7.5 \times 10^{-3}$ mol of Polymer Coupler Latex (B) prepared by Preparation Example 2.

Sample 12

63.9 ml of an aqueous solution of Polymer Coupler Latex (B) + 100 g of a 10% aqueous gelatin solution + 13 g of a dispersion containing Compound (8).

Sample 13

63.9 ml of an aqueous solution of Polymer Coupler Latex (B) + 110 g of a 10% aqueous gelatin solution.

Sample 14

A mixture composed of 10 g of 1-(2,4,6-trichlorophenyl)-3-[(2-chloro-5-tetradecanamido)anilino]-2-pyrazolin-5-one [Coupler a] as a comparative magenta coupler, 2 g of Compound (8), 14 ml of tricresyl phosphate and 30 ml of ethyl acetate was dissolved by heating on a steam bath and the solution was added to 100 ml of an aqueous solution containing 10 g of gelatin and 0.5 g of sodium dodecylbenzenesulfonate. The resulting mixture was then stirred using a homogenizer to prepare a coupler dispersion. The coupler dispersion was mixed with 100 g of the some silver chlorobromide emulsion used in the preparation of Samples 1 to 11 in Example 1 and then followed by the same procedure as described for Samples 1 to 11 in Example 1 to prepare Sample 14.

Sample 15

Sample 15 was prepared in the sama manner as described for Sample 14 except that Compound (8) was not added in the preparation of a coupler dispersion.

These samples were subjected to development processing in the same manner as described in Example 1 and then a fading test for 2 weeks using a day light type fluorescent lamp having an illumination of about 30,000 lux equipped with a filter capable of absorbing substantially all ultraviolet lights having a wavelength of 400 mµ or less. Thus the color image fastness and the formation of yellow stain in a low density portion were determined. The results thus obtained are shown in Table 2.

TABLE 2

| Sample | Color Fading Preventing Agent | Coupler | Color Image Fastness* $D_{1.0}$ | $D_{2.0}$ | Stain | Remarks |
|---|---|---|---|---|---|---|
| 12 | Compound (8) | Polymer Coupler Latex (B) | 10 | 9 | 0.11 | Present Invention |
| 13 | — | Polymer Coupler Latex (B) | 40 | 38 | 0.24 | Comparison |
| 14 | Compound (8) | Comparative Coupler a | 18 | 10 | 0.20 | Comparison |
| 15 | — | Comparative Coupler a | 25 | 21 | 0.23 | Comparison |

*Remaining amount of dye is shown in percentage.

From the results as shown in Table 2 above, it is apparent that the yellow stain preventing effect and the color image fastness improving effect are unusually large when compound (8) according to the present invention was applied to a polymer coupler latex in comparison with the case wherein Compound (8) according to the present invention was applied to a 3-anilino-5-pyrazolone type magenta coupler which is an oil-soluble magenta coupler described in Japanese Patent Application (OPI) No. 124141/80.

Further, the film strength of these samples was measured by the following method. The sample was immersed in water at 25° C. for 5 minutes. A needle having a steel ball (0.4 mm in radius) attached thereto was pressed against a surface of the sample and was moved parallel on the surface of the membrane at 5 mm/sec, with the load applied to the needle varying continuously in the range of from 0 to 200 g. The load that impaired the surface of the sample physically was measured. When the critical load of Sample 15 is taken as 100, those of Samples 12, 13 and 14 are 121, 128 and 95, respectively. This fact indicates that the film strength is improved in a sample in which a polymer coupler latex is used.

EXAMPLE 3

10 g of each of Compounds (1) and (8) according to the present invention and Comparative Compounds (b) and (f) was dissolved in 8 ml of tricresyl phosphate and 10 ml of ethyl acetate and the solution was added to 100 g of a 10% aqueous gelatin solution containing 0.5 g of sodium dodecylbenzenesulfonate. The resulting mixture was stirred using a homogenizer to prepare a dispersion.

Then, a mixture of 97 ml of Polymer Coupler Latex (B) prepared by Preparation Example 2 and 47.3 cc of a 100% aqueous gelatin solution or 105 g of Polymer Coupler Latex (E) prepared by Preparation Example 5, 15 g of the dispersion containing a color fading preventing agent prepared by the above described method and 100 g of silver halide emulsion containing $8.4 \times 10^{-2}$ mol of silver iodobromide (silver iodode: 4 mol%) and 10 g of gelatin were mixed in the combinations as shown in Table 3 below, and to the mixture was added 8 ml of a 4% acetone solution of 2-hydroxy-4,6-dichloro-s-triazine sodium salt. After adjusting the pH to 6.7, the mixture was coated on a cellulose triacetate film support in an amount of silver coated of $1.2 \times 10^{-3}$ mol/m$^2$ to prepare Samples 16 to 19 and 21 to 24.

Samples 20 and 25 were prepared in the same manner as described above except that a dispersion containing a color fading preventing agent was not added.

These films were exposed stepwise for sensitometry and then subjected to the following color development processing.

| Color Development Processing Step (38° C.) | |
| --- | --- |
| | Time (min) |
| 1. First development | 3 |
| 2. Washing with water | 1 |
| 3. Reversal | 2 |
| 4. Color development | 6 |
| 5. Stopping | 2 |
| 6. Bleaching | 6 |
| 7. Fixing | 4 |
| 8. Washing with water | 4 |
| 9. Stabilizing | 1 |
| 10. Drying | |

The processing solutions used in the color development processing had the following compositions:

| First Development Solution | | |
| --- | --- | --- |
| Water | 800 | ml |
| Sodium Tetrapolyphosphate | 2.0 | g |
| Sodium Hydrogen Sulfite | 8.0 | g |
| Sodium Sulfite | 37.0 | g |
| 1-Phenyl-3-pyrazolidone | 0.35 | g |
| Hydroquinone | 5.5 | g |
| Sodium Carbonate Monohydrate | 28.5 | g |
| Potassium Bromide | 1.5 | g |
| Potassium Iodide | 13.0 | mg |
| Sodium Thiocyanate | 1.4 | g |
| Water to make | 1 | liter |
| Reversal Solution | | |
| Water | 800 | ml |
| Hexasodium Nitrilo-N,N,N—trimethylene Phosphonate | 3.0 | g |
| Stannous Chloride Dihydrate | 1.0 | g |
| Sodium Hydroxide | 8.0 | g |
| Glacial Acetic Acid | 15.0 | ml |
| Water to make | 1 | liter |
| Color Development Solution | | |
| Water | 800 | ml |
| Sodium Tetrapolyphosphate | 2.0 | g |
| Benzyl Alcohol | 5.0 | ml |
| Sodium Sulfite | 7.5 | g |
| Trisodium Phosphate (12 hydrate) | 36.0 | g |
| Potassium Bromide | 1.0 | g |
| Potassium Iodide | 90.0 | mg |
| Sodium Hydroxide | 3.0 | g |
| Citrazic Acid | 1.5 | g |
| 4-Amino-3-methyl-N—ethyl-N—(β-hydroxyethyl)-aniline Sesquisulfate Monohydrate | 11.0 | g |
| Ethylenediamine | 3.0 | g |
| Water to make | 1.0 | liter |
| Stopping Solution | | |
| Water | 800 | ml |
| Glacial Acetic Acid | 5.0 | ml |
| Sodium Hydroxide | 3.0 | g |
| Dimethylaminoethaneisothiourea Dihydrochloride | 1.0 | g |
| Water to make | 1 | liter |
| Bleaching Solution | | |
| Water | 800 | ml |
| Sodium Ethylenediaminetetraacetate Dihydrate | 2.0 | g |
| Ammonium Iron (II) Ethylenediaminetetraacetate Dihydrate | 120.0 | g |
| Potassium Bromide | 100.0 | g |
| Water to make | 1 | liter |
| Fixing Solution | | |
| Water | 800 | ml |
| Ammonium Thiosulfate | 80.0 | g |
| Sodium sulfite | 5.0 | g |
| Sodium Hydrogen sulfite | 5.0 | g |
| Water to make | 1 | liter |
| Stabilizing Bath | | |
| Water | 800 | ml |
| Formalin (37 wt % formaldehyde) | 5.0 | ml |
| Fuji Driwell | 5.0 | ml |
| Water to make | 1.0 | liter |

Each of Samples 16 to 25 thus-processed was measured with the fastness of magenta color image when the sample was exposed to a day light type fluorescent lamp having an illumination of about 20,000 lux equipped with a filter capable of absorbing substantially all ultraviolet lights having a wavelength of 400 mμ or less for 2 weeks. The color image fastness was evaluated by calculating a rate of color density decrease (%) after the above described fading test at an area having a magenta initial density of 2.0. The results thus obtained are shown in Table 3 below.

TABLE 3

| Sample | Polymer Coupler Latex | Color Fading Preventing Agent | Color Image Fastness $D_{2.0}$ | Remarks |
| --- | --- | --- | --- | --- |
| 16 | (B) | Compound (1) | 14 | Present Invention |
| 17 | (B) | Compound (8) | 15 | Present Invention |
| 18 | (B) | Comparative Compound (b) | 28 | Comparison |
| 19 | (B) | Comparative Compound (f) | 25 | Comparison |
| 20 | (B) | — | 30 | Comparison |
| 21 | (E) | Compound (1) | 13 | Present Invention |
| 22 | (E) | Compound (8) | 15 | Present Invention |
| 23 | (E) | Comparative Compound (b) | 24 | Comparison |
| 24 | (E) | Comparative Compound (f) | 24 | Comparison |
| 25 | (E) | — | 31 | Comparison |

From the results as shown in Table 3 above, it is apparent that the p-alkoxyphenols in which tertiary alkyl groups are present at both the 2-position and the 5-position according to the present invention provide remarkably large light fastness improving effect in comparison with the comparative compounds.

EXAMPLE 4

10 g of each of Compounds (8) and (16) according to the present invention and Comparative Compound (e) was dissolved in 8 ml of tricresyl phosphate and 10 ml of ethyl acetate and the solution was added to 100 g of a 10% aqueous gelatin solution containing 0.5 g of sodium dodecylbenzenesulfonate. The resulting mixture was stirred using a homogenizer to prepare a dispersion.

Then, a mixture of 39 ml of Polymer Coupler Latex (D) prepared by Preparation Example 4 and 25.4 cc of a 10% aqueous gelatin solution or 56.5 g of Polymer Coupler Lates (F) prepared by Preparation Example 6, 10 g of the dispersion containing a color fading preventing agent prepared by the above described methods and 100 g of silver halide emulsion containing $5.6 \times 10^{-2}$ mol of silver iodobromide emulsion and 8 g of gelatin were mixed in the combination as shown in Table 4 below. To the mixture was added 8 ml of a 4% acetone solution of 2-hydroxy-4,6-dichloro-s-triazine sodium salt. After adjusting the pH to 6.5, the mixture was coated on a cellulose triacetate film support having a subbing layer to prepare Samples 26 to 28 and 30 to 32.

Samples 29 and 33 were prepared in the same manner as described above except that a dispersion containing a color fading preventing agent was not added.

These films were exposed stepwise for sensitometry and then subjected to the following color development processing.

| Color Development Processing Step | Time | Temperature (°C.) |
|---|---|---|
| 1. Color development | 3 min 15 sec | 38 |
| 2. Bleaching | 6 min 30 sec | " |
| 3 Washing with water | 2 min | " |
| 4 Fixing | 4 min | " |
| 5. Washing with water | 4 min | " |
| 6. Stabilizing | 1 min | " |

The process solutions used in the color development processing had the following compositions:

| Color Developer Solution | | |
|---|---|---|
| Water | 800 | ml |
| 4-(N—Ethyl-N—hydroxyethyl)amino-2-methylaniline Sulfate | 5 | g |
| Sodium Sulfite | 5 | g |
| Hydroxylamine Sulfate | 2 | g |
| Potassium Carbonate | 30 | g |
| Potassium Hydrogen Carbonate | 1.2 | g |
| Potassium Bromide | 1.2 | g |
| Sodium Chloride | 0.2 | g |
| Trisodium Nitrilotriacetate | 1.2 | g |
| Water to make | 1 | liter |
| | (pH 10.1) | |
| Bleaching Solution | | |
| Water | 800 | ml |
| Iron (III) Ammonium Ethylenediamine-tetraacetate | 100 | g |
| Disodium Ethylenediaminetetraacetate | 10 | g |
| Potassium Bromide | 150 | g |
| Acetic Acid | 10 | g |
| Water to make | 1 | liter |
| | (pH 6.0) | |
| Fixing Solution | | |
| Water | 800 | ml |
| Ammonium Thiosulfate | 150 | g |
| Sodium Sulfite | 10 | g |
| Sodium Hydrogen Sulfite | 2.5 | g |
| Water to make | 1 | liter |
| | (pH 6.0) | |
| Stabilizing Bath | | |
| Water | 800 | ml |
| Formalin (37 wt % formaldehyde) | 5 | ml |
| Driwell | 3 | ml |
| Water to make | 1 | liter |

Each of Samples 26 to 33 thus processed was measured with the fastness of magenta color image when the sample was exposed to a day light type fluorescent lamp having an illumination of 20,000 lux equipped with a filter capable of absorbing substantially all ultraviolet lights having a wavelength of 400 mµ or less for 1 week. The results thus obtained are shown in Table 4 below.

TABLE 4

| Sample | Polymer Coupler Latex | Color Fading Preventing Agent | Color Image Fastness $D_{1.0}$ | Remarks |
|---|---|---|---|---|
| 26 | (D) | Compound (8) | 12 | Present Invention |
| 27 | (D) | Compound (16) | 15 | Present Invention |
| 28 | (D) | Comparative Compound (e) | 30 | Comparison |
| 29 | (D) | — | 44 | Comparison |
| 30 | (F) | Compound (8) | 11 | Present Invention |
| 31 | (F) | Compound (16) | 13 | Present Invention |
| 32 | (F) | Comparative compound (e) | 32 | Comparison |
| 33 | (F) | — | 40 | Comparison |

From the results as shown in Table 4 above, it is apparent that the compounds according to the present invention provide remarkably large light fastness imprving effect in comparision with the comparative compound.

While the invention has been described in detail with reference to specific embodiments thereof, it will be apparent to one skilled in the art that various changes and modifications can be made therein without departing from the spirit and scope thereof.

What is claimed is:

1. A silver halide color photographic light-sensitive material, comprising: a magenta color image forming polymer coupler latex; and a compound represented by the following general formula (I)

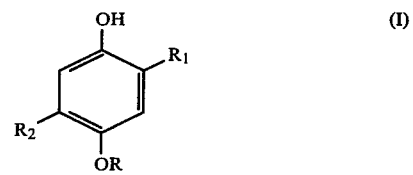

wherein R represents an alkyl group; and $R_1$ and $R_2$ each represents a tertiary alkyl group and $R_1$ and $R_2$ may be the same or different.

2. A silver halide color photographic light-sensitive material as claimed in claim 1, wherein the alkyl group represented by R is an alkyl group having from 1 to 25 carbon atoms.

3. A silver halide color photographic light-sensitive material as claimed in claim 1, wherein the tertiary alkyl group represented by $R_1$ or $R_2$ is a tertiary alkyl group having from 4 to 20 carbon atoms.

4. A silver halide color photographic light-sensitive material as claimed in claim 1, wherein a total number of the carbon atoms included in the alkyl groups represented by R, $R_1$ and $R_2$ is from 9 to 50.

5. A silver halide color photographic light-sensitive material as claimed in claim 1, wherein a total number of the carbon atoms included in the alkyl groups represented by R, $R_1$ and $R_2$ is from 10 to 40.

6. A silver halide color photographic light-sensitive material as claimed in claim 1, wherein an amount of the compound represented by the general formula (I) is in a range from 0.5 mol% to 200 mol% based on an amount of the coupler monomer included in the polymer coupler.

7. A silver halide color photographic light-sensitive material as claimed in claim 1, wherein an amount of the compound represented by the general formula (I) is in a range from 2 mol% to 100 mol% based on an amount of the coupler monomer included in the polymer coupler.

8. A silver halide color photographic light-sensitive material as claimed in claim 1, wherein the magenta polymer coupler latex is a polymer or copolymer having a repeating unit derived from a monomer represented by formula (II)

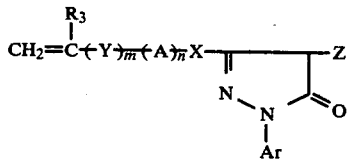
(II)

wherein R represents hydrogen, a lower alkyl group containing from 1 to 4 carbon atoms, or chlorine; X represents —CONH—, —NH—, —NHCONH— or —NHCOO—; Y represents —CONH— or —COO—; A represents an unsubstituted or substituted alkylene group or an unsubstituted or substituted phenylene group; Ar represents an unsubstituted or substituted phenyl group; Z represents a group which is directly bonded to the coupling position and is capable of being released upon the coupling reaction with an oxidation product of an aromatic primary amine developing agent; m represents 0 or 1; and n represents 0 or 1.

9. A silver halide color photographic light-sensitive material as claimed in claim 8, wherein the substituent for the alkylene group or the phenylene group represented by A is an aryl group, a nitro group, a hydroxy group, a cyano group, a sulfo group, an alkoxy group, an aryloxy group, an acyloxy group, an acylamino group, a sulfonamido group, a sulfamoyl group, a halogen atom, a carboxy group, a carbamoyl group, an alkoxycarbonyl group, or a sulfonyl group.

10. A silver halide color photographic light-sensitive material as claimed in claim 8, wherein the substituent for the phenyl group represented by Ar is an alkyl group, an alkoxy group, an aryloxy group, an alkoxycarbonyl group, an acylamino group, a carbamoyl group, an alkylcarbamoyl group, a dialkylcarbamoyl group, an arylcarbamoyl group, an alkylsulfonyl group, an arylsulfonyl group, an alkylsulfonamido group, an arylsulfonamido group, a sulfamoyl group, an alkylsulfamoyl group, a dialkylsulfamoyl group, an alkylthio group, an arylthio group, a cyano group, a nitro group, or a halogen atom.

11. A silver halide color photographic light-sensitive material as claimed in claim 8, wherein the substituent for the phenyl group represented by Ar is a halogen atom, an alkyl group, an alkoxy group, an alkoxycarbonyl group, or a cyano group.

12. A silver halide color photographic light-sensitive material as claimed in claim 8, wherein Ar represents a phenyl group in which an ortho position is substituted with a halogen atom, an alkyl group, or an alkoxy group.

13. A silver halide color photographic light-sensitive material as claimed in claim 8, wherein Z is hydrogen or a releasable group containing an oxygen atom, a nitrogen atom or a sulfur atom through which it is bonded to the coupling position.

14. A silver halide color photographic light-sensitive material as claimed in claim 13, wherein the group capable of being released is a group in which the oxygen atom, nitrogen atom or sulfur atom is bonded to an alkyl group, an aryl group, a sulfonyl group, a sulfinyl group, a carbonyl group, a phosphoric acid group, a thiocarbonyl group, a heterocyclic group or a cyano group.

15. A silver halide color photographic light-sensitive material as claimed in claim 13, wherein the group capable of being released is a 5-membered or 6-membered ring containing a nitrogen atom which is bonded to the coupling position.

16. A silver halide color photographic light-sensitive material as claimed in claim 8, wherein the polymer is a homopolymer.

17. A silver halide color photographic light-sensitive material as claimed in claim 8, wherein the polymer is a copolymer.

18. A silver halide color photographic light-sensitive material as claimed in claim 17, wherein the copolymer contains a repeating unit derived from a non-color forming monomer which does not couple with an oxidation product of an aromatic primary amine developing agent.

19. A silver halide color photographic light-sensitive material as claimed in claim 18, wherein the non-color forming monomer is an acrylic acid ester, an acrylic acid amide, a vinyl ester, an acrylonitrile, an aromatic vinyl compound, itaconic acid, citraconic acid, crotonic acid, vinylidene chloride, a vinyl alkyl ether, an ester of maleic acid, N-vinyl-2-pyrrolidone, N-vinyl pyridine, or 2- or 4-vinyl pyridine.

20. A silver halide color photographic light-sensitive material as claimed in claim 18, wherein the non-color forming monomer is an acrylic acid ester, a methacrylic acid ester or a maleic acid ester.

21. A silver halide color photographic light-sensitive material as claimed in claim 1, wherein the amount of the color forming portion in the polymer coupler latex is from 5% to 80% by weight.

22. A silver halide color photographic light-sensitive material as claimed in claim 21, wherein the gram number of the polymer coupler latex containing 1 mol of coupler monomer is from 250 to 3,000.

23. A silver halide color photographic light-sensitive material as claimed in claim 1, wherein the photographic light-sensitive material comprises a support having thereon at least one silver halide emulsion layer.

24. A silver halide color photographic light-sensitive material as claimed in claim 23, wherein the silver halide emulsion layer contains the magenta color image forming polymer coupler latex and the compound represented by the general formula (I).

25. A silver halide color photographic light-sensitive material as claimed in claim 24, wherein the silver halide emulsion layer is a green-sensitive silver halide emulsion layer.

* * * * *